(12) United States Patent
Banter (10) Patent No.: US 11,602,301 B2
(45) Date of Patent: Mar. 14, 2023

(54) WHEAL AND FLARE ANALYZING SYSTEM

(71) Applicant: C. Bruce Banter, Northville, MI (US)

(72) Inventor: C. Bruce Banter, Northville, MI (US)

( * ) Notice: Subject to any disclaimer, the term of this patent is extended or adjusted under 35 U.S.C. 154(b) by 0 days.

(21) Appl. No.: 17/830,843

(22) Filed: Jun. 2, 2022

(65) Prior Publication Data
US 2022/0409121 A1    Dec. 29, 2022

Related U.S. Application Data (63) Continuation-in-part of application No. PCT/US2022/024968, filed on Apr. 15, 2022, and a continuation-in-part of application No. 17/688,197, filed on Mar. 7, 2022, now Pat. No. 11,408,820.

(60) Provisional application No. 63/197,539, filed on Jun. 7, 2021, provisional application No. 63/188,125, filed on May 13, 2021.

(51) Int. Cl.
*A61B 5/00* (2006.01)
*A61B 5/01* (2006.01)

(52) U.S. Cl.
CPC .......... *A61B 5/411* (2013.01); *A61B 5/0075* (2013.01); *A61B 5/01* (2013.01); *A61B 5/445* (2013.01); *A61B 2560/0214* (2013.01); *A61B 2562/0271* (2013.01); *A61B 2562/046* (2013.01); *A61B 2562/166* (2013.01)

(58) Field of Classification Search
CPC ......... A61B 5/411; A61B 5/0075; A61B 5/01; A61B 5/445; A61B 2560/0214; A61B 2562/0271; A61B 2562/046; A61B 2562/166

USPC .......................................................... 356/301
See application file for complete search history.

(56) References Cited

U.S. PATENT DOCUMENTS

| 6,629,932 B2 | 10/2003 | Weber |
| 10,238,300 B2 | 3/2019 | Stepien |
| 10,932,727 B2 | 3/2021 | Newberry |
| 2010/0100160 A1 | 4/2010 | Edman |
| 2011/0144462 A1 | 6/2011 | Lifsitz |
| 2015/0238636 A1* | 8/2015 | Homyk ............... A61B 5/7435 600/317 |

(Continued)

FOREIGN PATENT DOCUMENTS

| KR | 10-1657953 | 9/2016 |
| WO | PCT/EP2019/060315 | 11/2019 |
| WO | PCT/KR2019/015525 | 5/2020 |

*Primary Examiner* — Md M Rahman
(74) *Attorney, Agent, or Firm* — Gerald R. Black, Esq.

(57) ABSTRACT

The wheal and flare analyzing system analyzes the mast cell reaction to an allergen being administered in a scratch or prick skin test. The system comprises a sensor array and a processing unit. The sensor array includes a plurality of emitters surrounding a receiver at the allergen test site. Energy of various wavelengths is emitted into the allergen test site. An energy receiver measures reflected various wavelengths from the plurality of emitters. A microprocessor is in digital communication with the plurality of emitters and the energy receiver. The reflected wavelengths have an energy return indicative of the intensity of the allergic reaction in the mast cells. The intensity of the allergic reaction is analyzable from the reflected wavelengths and other data over time. A plurality of temperature sensors measuring local dermal temperatures surrounding the sensor array, the local dermal temperature being indicative of the intensity of the allergic reaction.

20 Claims, 11 Drawing Sheets

WHEAL AND FLARE ANALYZING SYSTEM

(56) References Cited

U.S. PATENT DOCUMENTS

2017/0322084 A1\* 11/2017 Haider ..................... G01J 3/42

\* cited by examiner

Fig. 2B

25 - Multiple Applicator Unit

Fig. 2C

22 - Wheal

25 - Multiple Applicator Unit
28 - Applicator Tip
29 - Reservoir
26 - Fluid Tray

Fig. 2A
PRIOR ART

Fig. 4
WHEAL AND FLARE ANALYZING SYSTEM

Fig. 5

Fig. 6B
SENSOR ARRAY

Fig. 6A
SENSOR ARRAY

Fig. 7
REACTION SEVERITY PLOT

Fig. 8
SENSOR and TEST SITE ALIGNMENT

Fig. 10
PROCESS FLOW DIAGRAM

WHEAL AND FLARE ANALYZING SYSTEM

CROSS-REFERENCE TO RELATED APPLICATIONS

This application is a continuation-in-part of and claims priority to U.S. Provisional Application No. 63/197,539, entitled "Wheal and Flare Analyzing System" (Banter), filed on Jun. 7, 2021; PCT Application No. PCT/US22/24968, entitled "Produce Freshness Sensor" (Banter), filed on Apr. 15, 2022; U.S. patent application Ser. No. 17/688,197, entitled "Produce Freshness Sensor" (Banter), filed on Mar. 7, 2022; and U.S. Provisional Application No. 63/188,125, entitled "Produce Freshness Sensor" (Banter), filed on May 13, 2021.

FIELD OF THE INVENTION

The present invention relates generally to systems and methods providing information to medical professionals for use in evaluating patient reactions to allergens during skin testing as the reactions occur.

BACKGROUND OF THE INVENTION

Allergy skin testing is used to determine whether an individual is allergic to a particular substance. A person often seeks allergy testing if she is experiencing allergy symptoms but does not know which allergen is causing the symptoms.

Allergy testing involves subjecting a patient to a wide variety of different allergens to determine which allergens cause allergic reactions in the patient. Such testing requires that the allergen is applied beneath the surface of the patient's skin. There are two methods of intracutaneous allergen application, the "prick or puncture" method and the "scratch or abrasion" method. In the puncture method a sharply pointed needle or tine pierces the patient's skin, and a small amount of allergen is applied. In the abrasion method a needle, tine, or other sharp object pierces the patient's skin and moves laterally after the initial piercing forming a scratch or an abrasion.

A health care provider observes the pierced area and diagnoses an allergy based on swelling, redness, or other signs of reaction. A health care provider then observes the injection site for an allergic reaction.

Sampling and testing of bodily fluids (e.g., saliva, blood, urine, fecal matter, foods, plants, fish, minerals, animals, etc.) is common for any number of biochemical or physiological conditions to determine the general state of health of a human or animal.

The prior art reporting is primarily directed at reporting, identifying, and preventing allergic reactions.

U.S. Pat. No. 7,420,663 (Wang; et al.) is for a spectroscopic sensor on a mobile phone. The spectroscopic sensor is integrated into a mobile communication device, such as a mobile phone. The spectroscopic sensor measures the optical spectra of a physical object for purposes of detection, identification, authentication, and real time monitoring. Through the mobile communication device, the spectral information is transmitted, distributed, collected, and shared by using all the functions of the known or existing wireless communication networks.

U.S. patent application Ser. No. 15/556,316 (Cronin; et al.) discloses software for providing health information to a user expressing symptoms of an allergic reaction via a wearable device. The system acquires in real-time, substantiating feedback of indicators of allergic reaction conditions and no automatic and immediate remedial measures by commencing an interactive question and answer session with the user at the inception of detection of the condition and providing health information that is helpful to the user in remedying the condition. The question-and-answer session facilitates the determination of the cause and severity of the allergic reaction.

U.S. patent application Ser. No. 10/554,532 (Iida; et al.) discloses a diagnostic support system and mobile terminal, which judge a morbidity possibility that a user holding the mobile terminal is suffering from a disease. The analytical center includes a unit which obtains symptom data representing the symptom of the user from the mobile terminal in correspondence with a position at which and a date on which the symptom data was made, a morbidity possibility calculation unit which judges the morbidity possibility that the user is suffering from the disease.

Wheals and flares are observed and analyzed by trained medical personnel to determine degrees of response and allergic reactions. Applications of saline and histamine are usually applied as controls for comparison to various allergen compounds. Single or multiple scratch applicators are used to apply the fluids into the patient's skin. Wheals and flares are formed within 10 to 15 minutes after application. Wheals are raised skin bumps and flares are discolorations around the wheal. The size of the wheals and flares are indicative of the degree of the allergic reaction. The sizes may be either visually estimated or measured.

What is needed is an improved allergen testing system that provides relevant information to medical professionals that witness patient reactions to allergens as the reactions are occurring.

What is needed is an improved allergen testing system that provides more data to the medical professional faster, that uses less allergen, that is compatible with puncture testing and scratch testing systems, that reduces the number of false negatives and is less painful to patients.

SUMMARY OF THE INVENTION

The wheal and flare analyzing system of the present invention addresses these needs.

The wheal and flare analyzing system of the present invention analyzes an allergic reaction in a mast cell to an allergen being administered in a skin test.

The basic components of the system for analyzing an allergic reaction within a mast cell comprise; a sensor array with multiple energy emitters and emitter light guides, and an energy receiver and receiver light guides, an Analog Front End (AFE), and a microprocessor.

The sensor array includes a first emitter that emits energy of a first wavelength into the skin of the patient via an emitter light guide. The sensor array also includes a second emitter that emits energy of a second wavelength into the skin of the patient via a second emitter light guide. The sensor array preferably includes a third emitter and light guide and a fourth emitter and light guide. The third emitter emits energy of a third wavelength into the skin of the patient via the third emitter light guide, and the fourth emitter emits energy of a fourth wavelength into the skin of the patient via a fourth emitter light guide.

The microprocessor is in digital communication with the AFE to sequentially control the four emitters and process the energy from the energy receiver. An energy return of the first reflected wavelength, the second reflected wavelength, the third reflected wavelength, and the fourth reflected wavelength are indicative of the intensity of the allergic reaction of the allergen applied to the site in the mast cells.

The energy receiver and its light guide are preferably positioned in the center of the array with the emitters and their lights guide around the center. The energy receiver and center of the array are preferably positioned proximate to the center of the site where the allergen is introduced into the mast cells. The energy receiver measures the first reflected wavelength from the first emitter, the second reflected wavelength from the second emitter, the third reflected wavelength from the third emitter, and the fourth reflected wavelength from the fourth emitter.

The reflected wavelengths have an energy return indicative of the intensity of the allergic reaction in the mast cells plus increased vasodilation and congestion. The intensity of the allergic reaction is analyzable from the reflected wavelength and other data over time.

A plurality of temperature sensors abuts the sensor array. The temperature sensors measure local dermal temperature. The temperature sensors are also linked to the microprocessor. The local dermal temperature is indicative of the intensity of the allergic reaction.

In a second preferred embodiment of the wheal and flare analyzing system of the present invention, the information from each of the sensor cells and the temperature measurement of the patient skin are communicated to an Application Program via a wired connection or wireless link for communication to a medical professional.

As used herein, "pierce and piercing" includes a penetration of the skin.

As used herein, "a scratch or abrasion" is a piercing of the skin caused by a sharp object, the sharp object moving laterally along the surface of the skin subsequent to the piercing. The piercing formed may be an arcuate line, a straight line, a closed arcuate shape, or a jagged arcuate line produced on the skin.

As used herein, "a puncture or a prick" is a piercing of the skin made with a sharp object that generates a hole penetrating the skin. The piercing includes a wound made by a needle or tine applied into the skin, including a gouge. The sharp object does not move laterally relatively to the surface of the skin subsequent to the initial piercing.

As used herein, "a puncture or a prick" and "a scratch or abrasion" are mutually exclusive.

Still other objectives of the processes for wheal and flare analyzing system of the present invention will become apparent to those skilled in this art from the following description wherein there is shown and described in the preferred embodiment of this invention, simply by the way of illustration of the best modes contemplated for carrying out the present disclosure. As will be realized, the present disclosure is capable of different embodiments, and its several details are capable of modification in various, obvious aspects all without departing from the invention. Accordingly, the drawings and descriptions will be regarded as illustrative in nature and not as restrictive.

BRIEF DESCRIPTION OF THE DRAWINGS

FIGS. 6A and 6B depict a pair of end views of simplified schematics of the sensory array of the wheal and flare analyzing system of FIG. 3. In FIG. 6A the microprocessor commands the AFE/LED drivers to power the first wavelength emitter LED to emit energy via the light guide emitter and looks for energy return via the light guide receiver at the receiver, the emitted energy being either reflected or absorbed by the surface and underlaying material of the mast cells. In FIG. 6B the microprocessor commands the AFE/LED drivers to power the second wavelength emitter LED to emit energy via the light guide emitter and looks for energy return via the light guide receiver at the receiver, the emitted energy being either reflected or absorbed by the surface and underlaying material of the mast cells.

DETAILED DESCRIPTION OF THE PREFERRED EMBODIMENTS

Figure 1A:
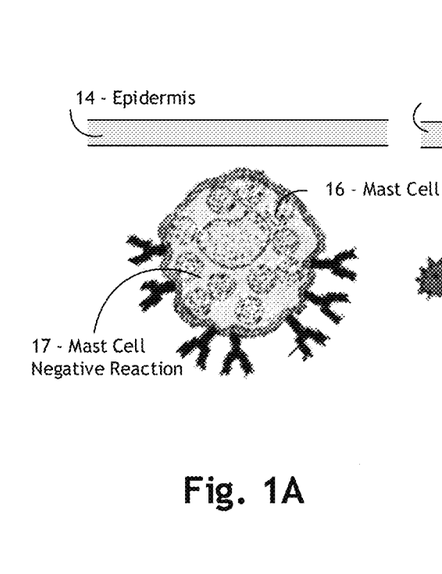
FIG. 1A depicts a healthy mast cell beneath the epidermis of a patient for use in allergy skin testing.

Referring now to the drawings, FIG. 1A depicts a healthy mast cell [16] beneath the epidermis [14] of a patient for use with the wheal and flare analyzing system of the present invention [10].

For allergies to initially develop, the body must be exposed to something in the environment, an allergen, which prompts the body to initiate an immune response. Mast cells reside within body tissues. For an individual with an allergy to a specific allergen, when an allergen enters the immune system, the allergen binds to the surface of these mast cells causing the mast cells to break down or degranulate. As degranulation occurs, the mast cell releases a series of chemicals that orchestrate the allergic reaction. The best known of these chemicals is histamine. The immediate skin reaction reaches a peak in 10 to 15 minutes and consists of a pale central area surrounded by redness and swelling (a wheal). This allergic reaction [19] is depicted in FIGS. 1B and 1C.

Figures 1B, 1C:
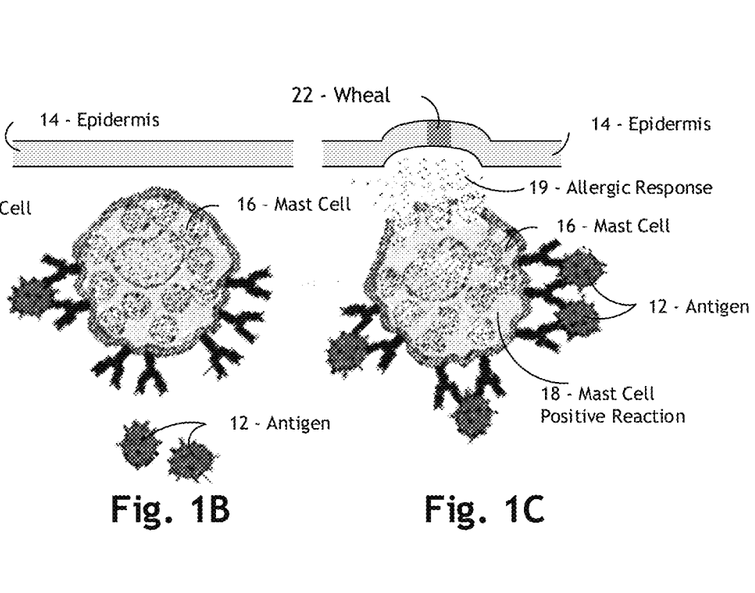
FIG. 1B depicts the healthy mast cell beneath the epidermis of a patient of FIG. 1A under attack by a plurality of antigens.
FIG. 1C depicts the mast cell of FIG. 1A in a full-blown allergic reaction by the release of histamines and other chemicals to protect the mast cell, resulting in a noticeable wheal formed on the epidermis of the patient.

FIG. 1B depicts the healthy mast cell beneath the epidermis [14] of a patient of FIG. 1A under attack by a plurality of antigens, and FIG. 1C depicts a full-blown allergic reaction [19] in the mast cell [16] of FIG. 1A by the release of histamines and other chemicals to protect the mast cell [16], resulting in a noticeable wheal [22] formed on the epidermis [14] of the patient.

Some people also experience a late phase reaction. The tissues where mast cells have released chemicals may become hot, tender, red, and swollen for hours. It is the onset and complexity of this reaction that many people experience to these allergens as the reactions are occurring that the wheal and flare analyzing system of the present invention [10] captures.

Figures 2A, 2B, 2C:
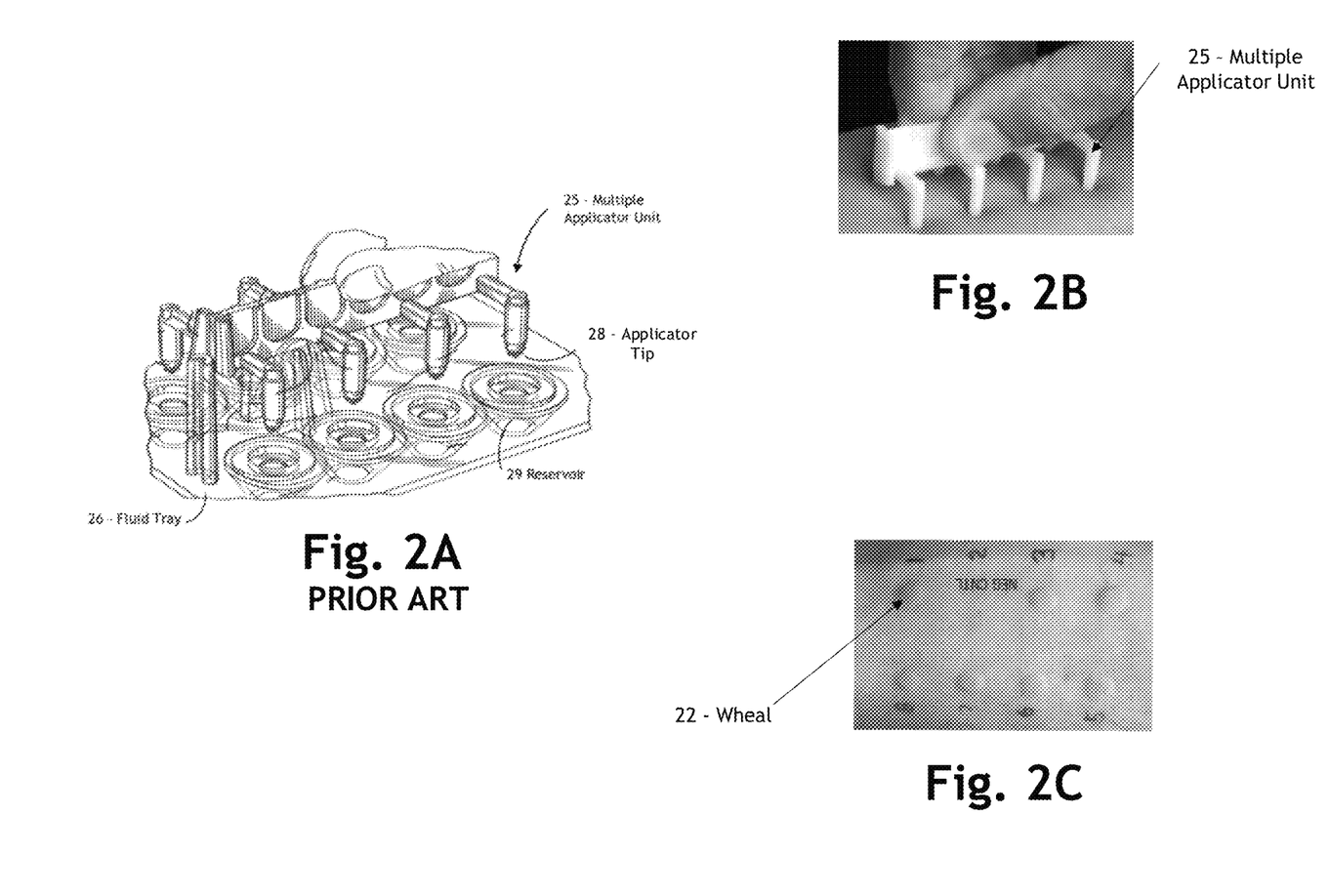
FIG. 2A depicts a prior art allergy testing system comprising a multiple applicator unit disposed relative to a fluid tray. The multiple applicator unit has a grip portion for holding the device. One or more legs extend from the grip, and each leg is oriented to interact with a well containing a potential allergen. Each leg has a test head, and each test head has a plurality of elongated spike members. The elongated spike members have a sharp end configured to receive the potential allergen from a well in the fluid tray and to puncture the skin of the patient being tested skin.
FIG. 2B depicts the multiple applicator unit of FIG. 2A being applied onto a patient's skin for allergy skin testing.
FIG. 2C depicts the skin of the patient after the multiple applicator unit of FIG. 2B has been removed from the patient's skin, with markings to denote the individual test sites and reference to the allergens applied at each individual test site.

FIG. 2A depicts a prior art allergy testing system comprising a multiple applicator unit [25] disposed relative to a fluid tray [26]. The multiple applicator test unit [25] is known in the prior art (see U.S. Pat. No. 8,469,900). The multiple applicator unit [25] has a grip portion for holding the device. One or more legs extend from the grip portion, and each leg is oriented to interact with a reservoir containing a potential allergen. Each leg has a test head [28] or tip, and each test head [28] has a plurality of elongated spike members. The elongated spike members have a sharp end configured to receive the potential allergen from a well and to puncture the skin of the patient being tested.

FIG. 2B depicts the multiple applicator unit [25] of FIG. 2A being applied to a test site onto a patient's skin for allergy skin testing. FIG. 2C depicts the skin of the patient after the multiple applicator unit [25] of FIG. 2B has been removed from the test site, with markings on the patient's skin to denote the individual test sites and reference to the allergens applied at each individual site. A wheal [22] is shown at one of the test sites on the patient's skin. After removal of the applicator [25] each of the individual test sites are marked with numbers or symbols to reference each test site to the applied specific allergen.

Figure 3:
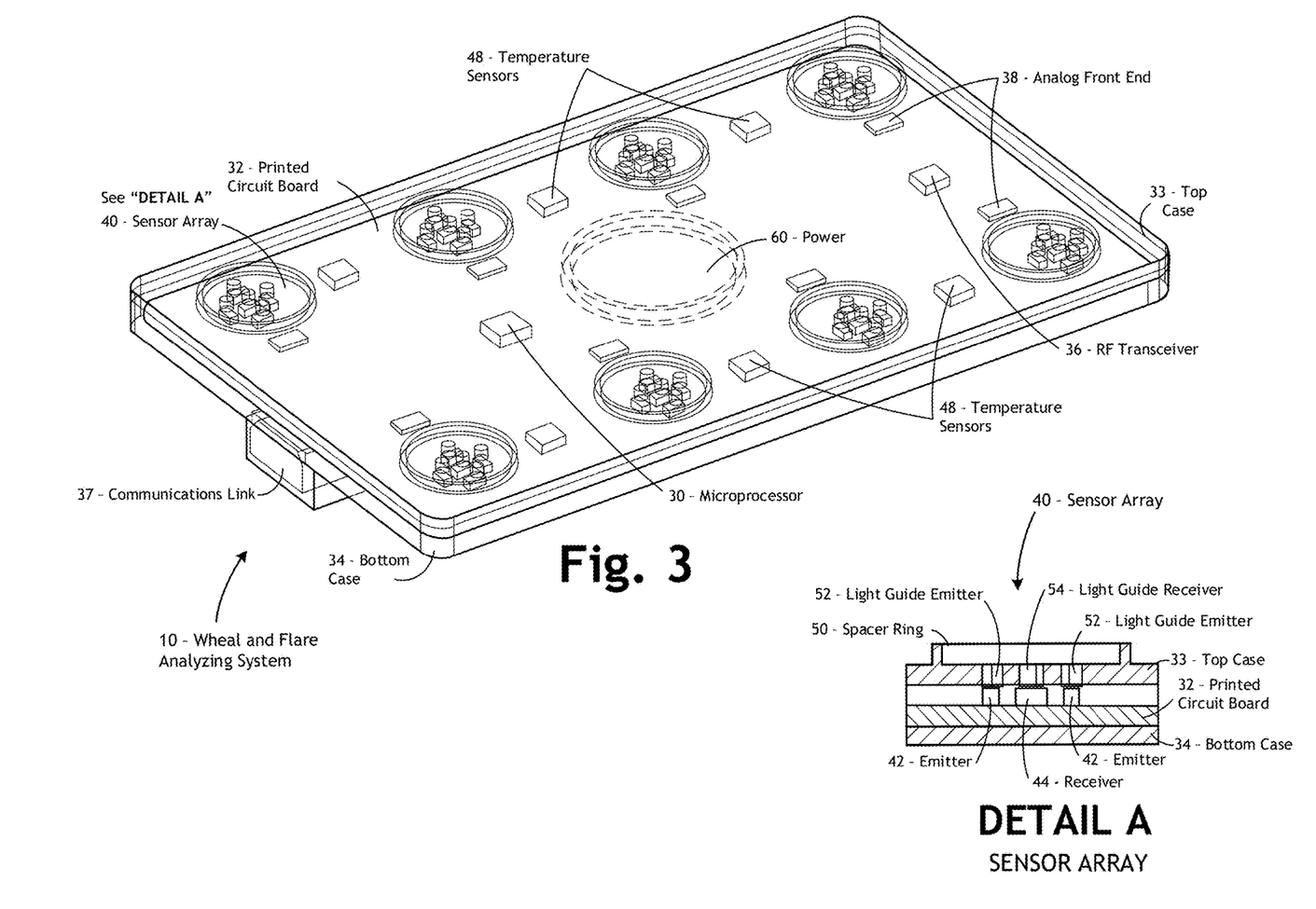
FIG. 3 depicts an assembly view of the first preferred embodiment of the wheal and flare analyzing system of the present invention, the system including a microprocessor, six temperature sensors, eight sensor arrays, eight (8) AFE/LED drivers, an rf transceiver, a communications link, and a power source, all mounted relative to a printed circuit board and encapsulated. "DETAIL A" is an exploded end view of a sensor array of the wheal and flare analyzing system of FIG. 3.

FIG. 3 depicts an assembly view of the first preferred embodiment of the wheal and flare analyzing system [10] of the present invention. The basic components of the system for analyzing an allergic reaction [10] within a mast cell comprise a sensor array [40] comprising an energy receiver [44], receiver light guide [54], emitters [42], emitter light guide [52]; analog front ends (AFE) [38]; and a microprocessor [30]. A space ring [50] provides an air gap with the patient's skin.

The sensor array [40] includes a first emitter [42] that emits energy of a first wavelength into the skin of the patient via a first light guide emitter [52]. The sensor array [40] also includes a second emitter [42] that emits energy of a second wavelength into the skin of the patient via a second light guide emitter [52]. The sensor array preferably includes a third emitter [42] and third light guide emitter [52], a fourth emitter [42] and fourth light guide emitter [52], the third emitter emitting energy of a third wavelength into the skin of the patient via a third light guide emitter [52], the fourth emitter emitting energy of a fourth wavelength into the skin of the patient via a fourth light guide emitter [52]. The sensor array [40] includes a spacer ring [50] that is on the outer periphery of the sensor array and provides an air gap with the patient's skin. The microprocessor [30] is in digital communication with the AFE [38] that controls all four emitters [42] and processes the energy from the energy receiver [44]. An energy return of the first reflected wavelength, the second reflected wavelength, the third reflected wavelength, and the fourth reflected wavelength are indicative of the intensity of the allergic reaction of the allergen applied to the site in the mast cells.

The energy receiver [44] and its light guide [54] are preferably positioned in the center of the array with the emitters [42] and their lights guides [52] around the center and energy receiver [44]. The energy receiver [44] is preferably positioned proximate to the center of the site where the allergen is introduced into the mast cells. The energy receiver [44] via the light guide receiver [54] measures the first reflected wavelength from the first emitter [42] via the light guide emitter [52], the second reflected wavelength from the second emitter [42] via the light guide emitter [52], the third reflected wavelength from the third emitter [42] via the light guide emitter [52], and the fourth reflected wavelength from the fourth emitter [42] via the light guide emitter [52].

DETAIL A depicts a cross section view of the sensor array [40] of the first preferred embodiment of the wheal and flare analyzing system [10] of FIG. 3.

Figure 4:
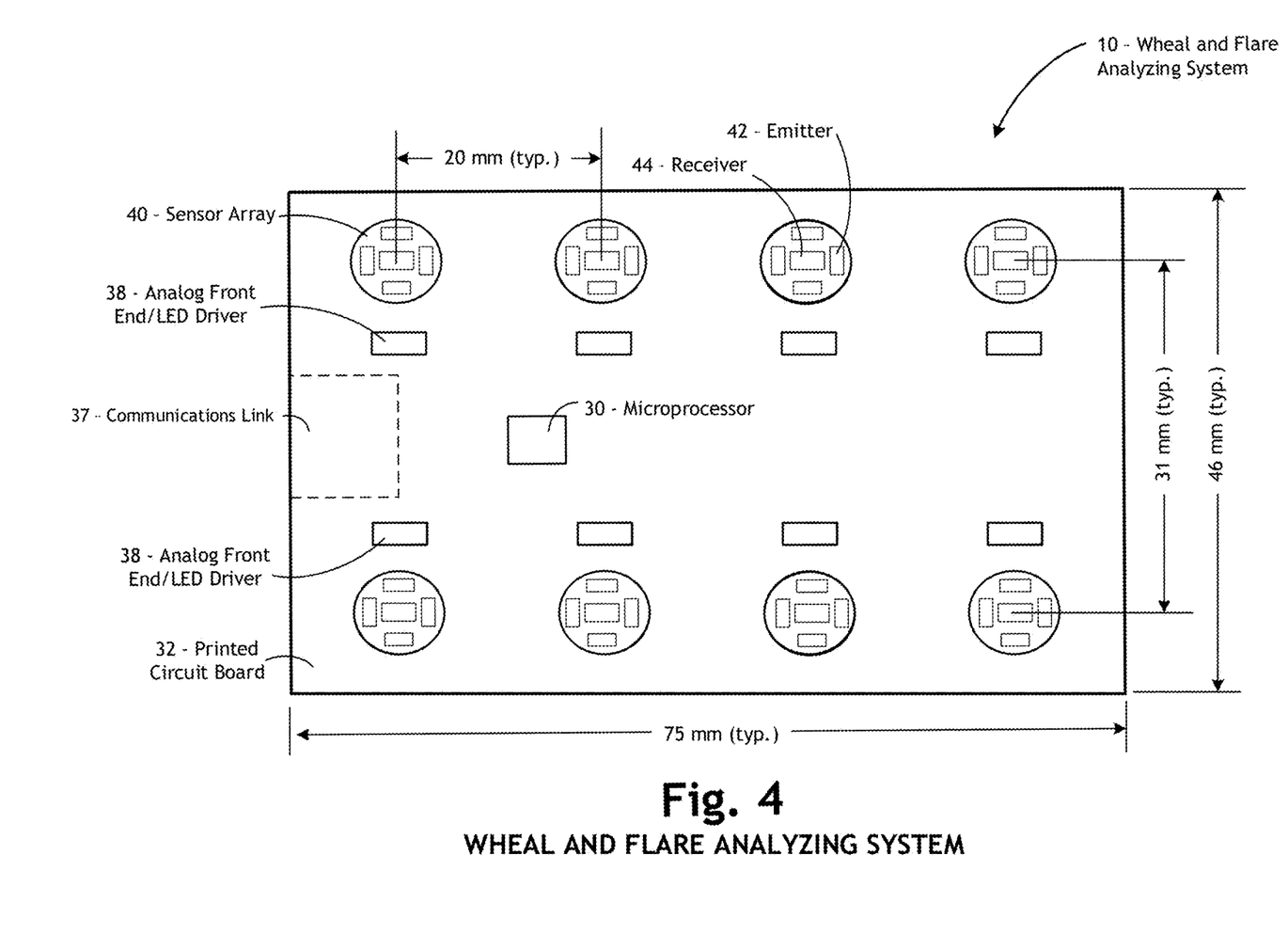
FIG. 4 depicts the wheal and flare analyzing system FIG. 3 with eight (8) sensor arrays on a printed circuit board, with the preferred typical dimensions of the unit and the sensor arrays which need to align and be compatible with the multiple applicator unit used in the test (see FIG. 2A). A spacer ring as part of the sensor array creates space between the sensor array and the patient's skin to enable the wheal and flare to form. It also minimizes sensor contact with the patient's skin to minimize influencing the temperature of the patient's skin at the test site.

FIG. 4 depicts the wheal and flare analyzing system of FIG. 3 with eight (8) sensor arrays on a printed circuit board, the sensor arrays, with preferred typical dimensions of the unit and the sensor arrays which need to align and be compatible with the multiple applicator unit used in the allergy skin test (see FIG. 2A). A spacer ring as part of the sensor array creates space between the sensor array and the patient's skin to enable the wheal and flare to form. It also minimizes sensor contact with the patient's skin to minimize influencing the temperature of the patient's skin at the test site.

Figure 5:
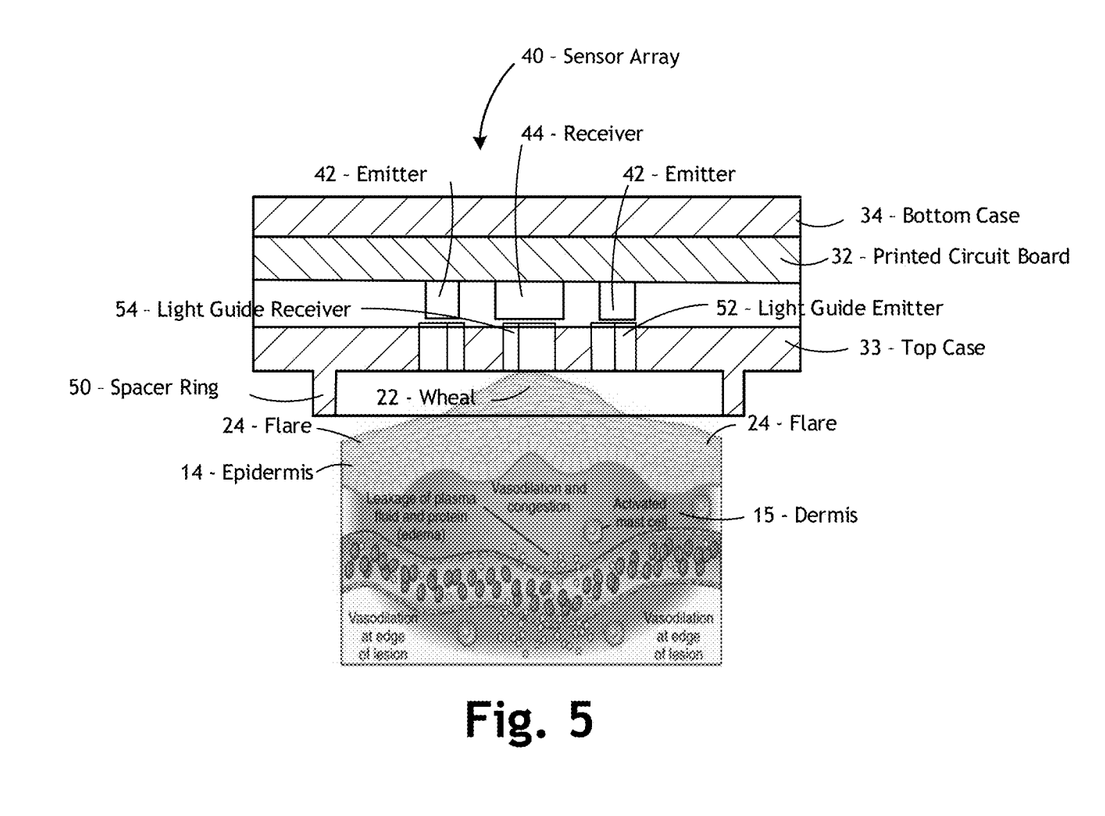
FIG. 5 depicts the sensor array of DETAIL A of FIG. 3 of the wheal and flare analyzing system of the present invention disposed on the skin of a patient.

FIG. 5 depicts the sensor array [40] of the first preferred embodiment of the wheal and flare analyzing system of the present invention [10] positioned on the skin of a patient at a test site. A noticeable wheal [22] has formed on the epidermis [14] of the patient, the wheal [22] being sandwiched between a pair of flares [24].

A cross section of a sensor array [40] with a spacer ring [50], the spacer ring [50] creating space between the sensor array [40] and the patient's skin for the wheal [22] and the pair of flares [24] to form at the test site. The spacer ring [50] also reduces sensor contact with the skin to minimize influencing the temperature of the patient's skin at the test site.

The skin of the patient is depicted in an exploded view, as the activity occurring in the dermis tissue of the patient after the allergen has been inserted after a routine allergy skin test resulting in the formation of a wheal [22] in the center of the site and a flare [24] that extends on the outer periphery around the center of the wheal [22].

The wheal and flare analyzing system of the present invention [10] comprises a sensor array [40], analog front end [38], and a microprocessor [30]. The information from each of the sensor arrays [40] and the temperature measurement of the patient skin are communication to an Application Program via a wired connection [37] or a wireless link [36], from the microprocessor [30].

The sensory array [40] has a plurality of emitters [42] disposed about or preferably surrounding a receiver [44] and the analog front ends/LED drivers [38] at the allergen test site.

Energy is emitted of various wavelengths into the allergen test site. An energy receiver [44] adjacent to the allergen test site measures reflected wavelengths via the light guide receiver [54] from the plurality of emitters [42] via their light guides emitters [52]. The microprocessor [30] is in digital communication via the analog front end/LED drivers [38] with the plurality of emitters [42] and the energy receiver [44]. The reflected wavelengths have an energy return indicative of the intensity of the allergic reaction in the mast cells [16]. The intensity of the allergic reaction [19] is analyzable from the reflected wavelength and other data over time.

In one preferred embodiment, a plurality of temperature sensors (not shown) abuts the sensor array [40]. The temperature sensors measure local dermal temperature. The temperature sensors are also linked to the microprocessor [30]. The local dermal temperature is indicative of the intensity of the allergic reaction [19].

Figure 6A:
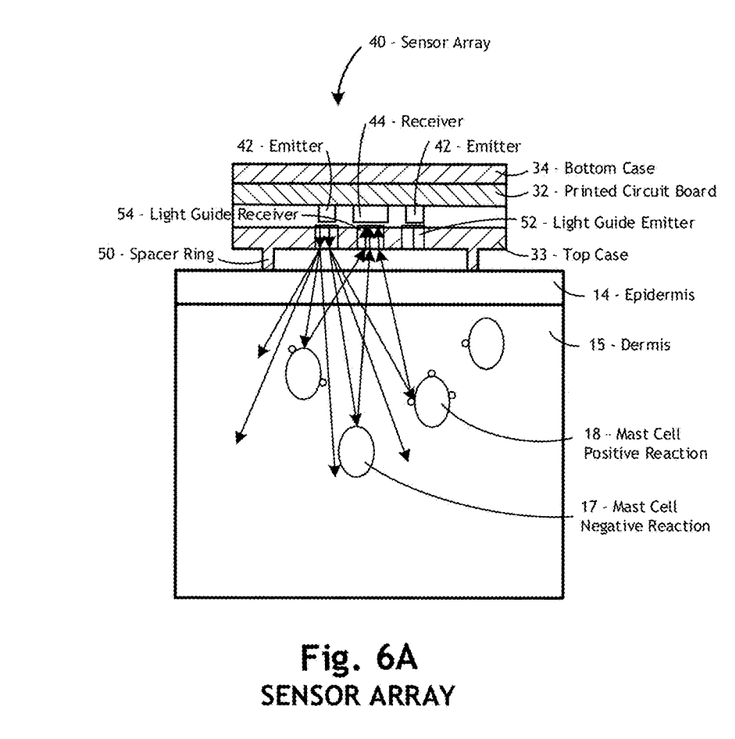
Figure 6B:
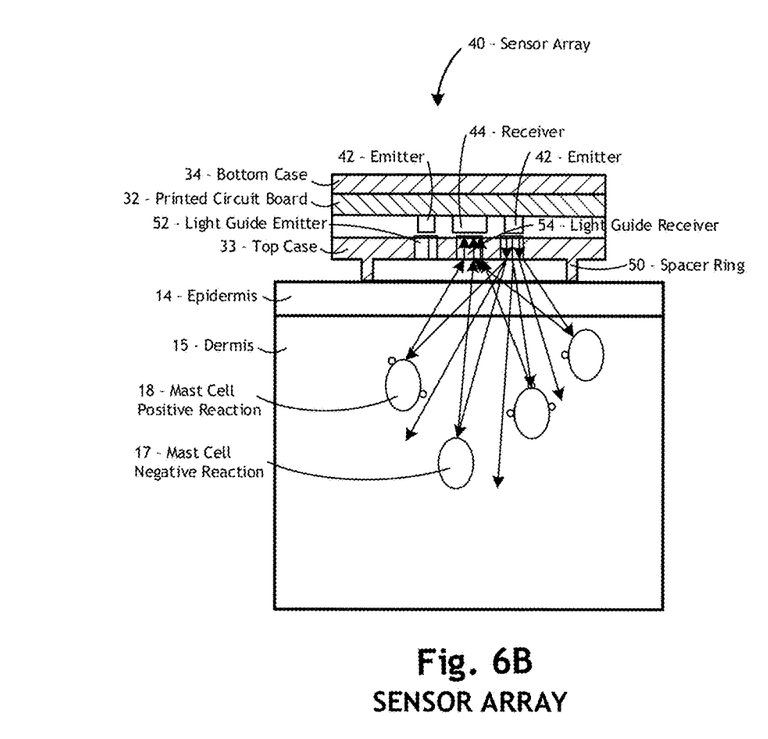

FIGS. 6A and 6B depict a pair of simplified top views the of the sensory array [40] of the wheal and flare analyzing system of the present invention [10]. The microprocessor [30] commands the LED drivers [38] to power the first wavelength LED to emit energy from the emitters [42] and look for energy return at the receiver [44], the emitted energy being either reflected or absorbed by the surface and underlaying material of the mast cells [16]. The process is repeated with the second wavelength LED.

Figure 7:
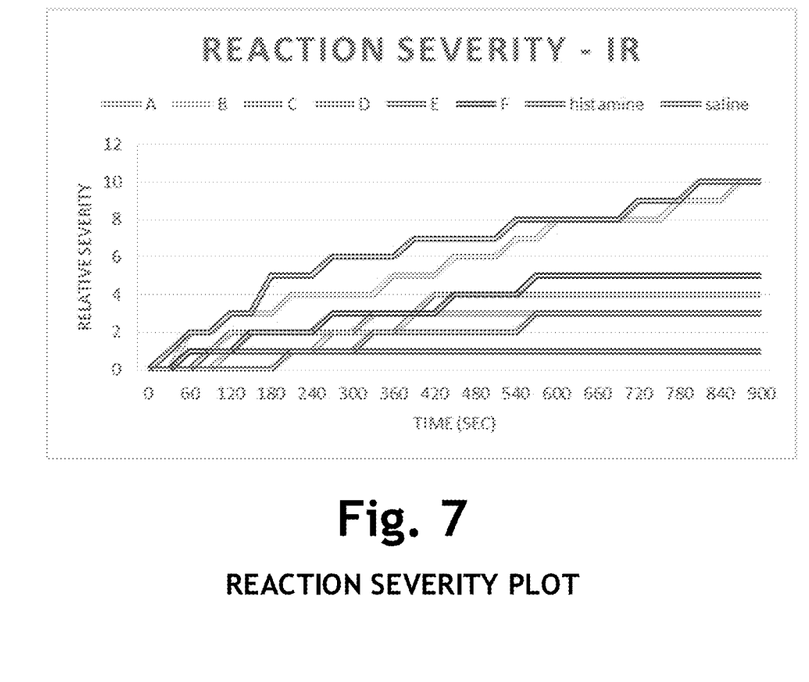
FIG. 7 depicts a plot of the reaction severity plot of one wavelength over time for eight (8) different fluids and test sites.

FIG. 7 depicts a plot of the Reaction Severity of one wavelength over time for eight (8) different fluids and test sites. Energy is preferably emitted from each emitter [42] in sequence and the reflected energy is measured by the centrally located receiver [44]. The energy wavelengths have unique energy returns depending on the interaction in the tissues. The amount of mast cells [16], proteins, and fluids can be detected by analyzing the energy returns over time to calculate a Relative Severity. The allergic reaction for each allergen is also compared to the reactions for saline (negative reaction) and histamine (positive reaction).

Figure 8:
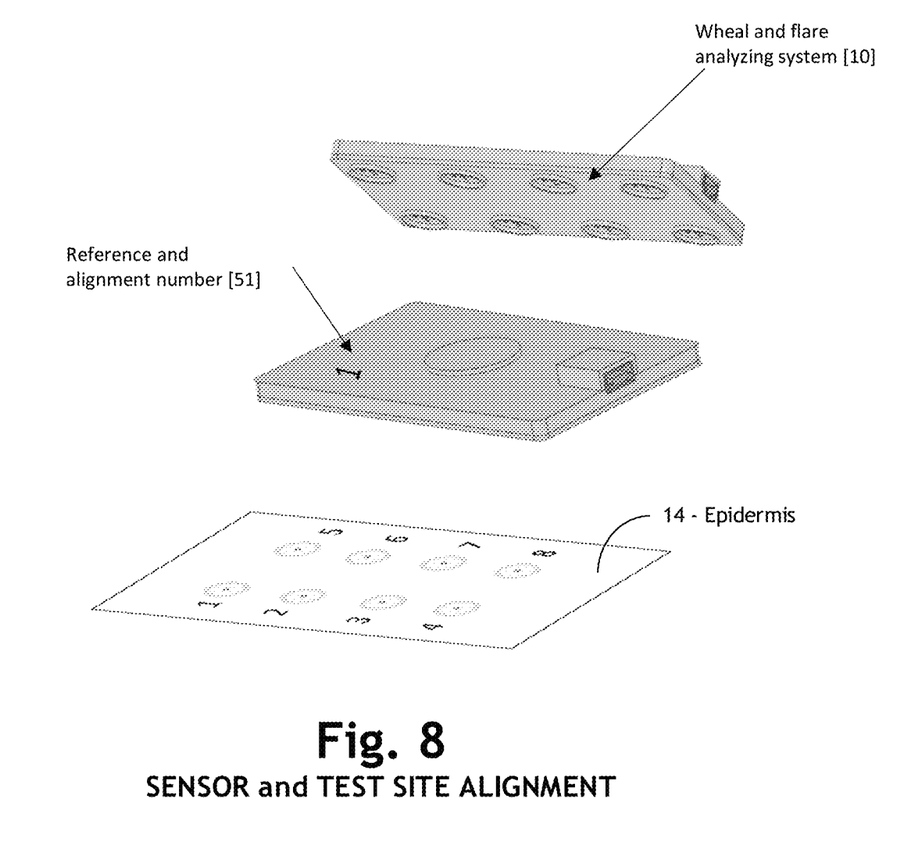
FIG. 8 depicts a simplified sensor and test site alignment for the first preferred embodiment of the wheal and flare analyzing system of FIG. 3, depicting the markings on the patient's skin to denote the individual test sites and reference to the allergens applied at each individual site.

FIG. 8 depicts the attachment of the wheal and flare analyzing system [10] to the marked test sites on the patient's skin from FIG. 2B. The wheal and flare analyzing system [10] is aligned with the numbers or symbols for the individual test sites. A reference and alignment number [51] is marked on the top of the wheal and flare analyzing system [10] to align with the marked number or symbol for the first individual test site on the patient's skin. The markings on the patient's skin denote the individual test sites and reference to the allergens applied at each individual site.

Figure 9:
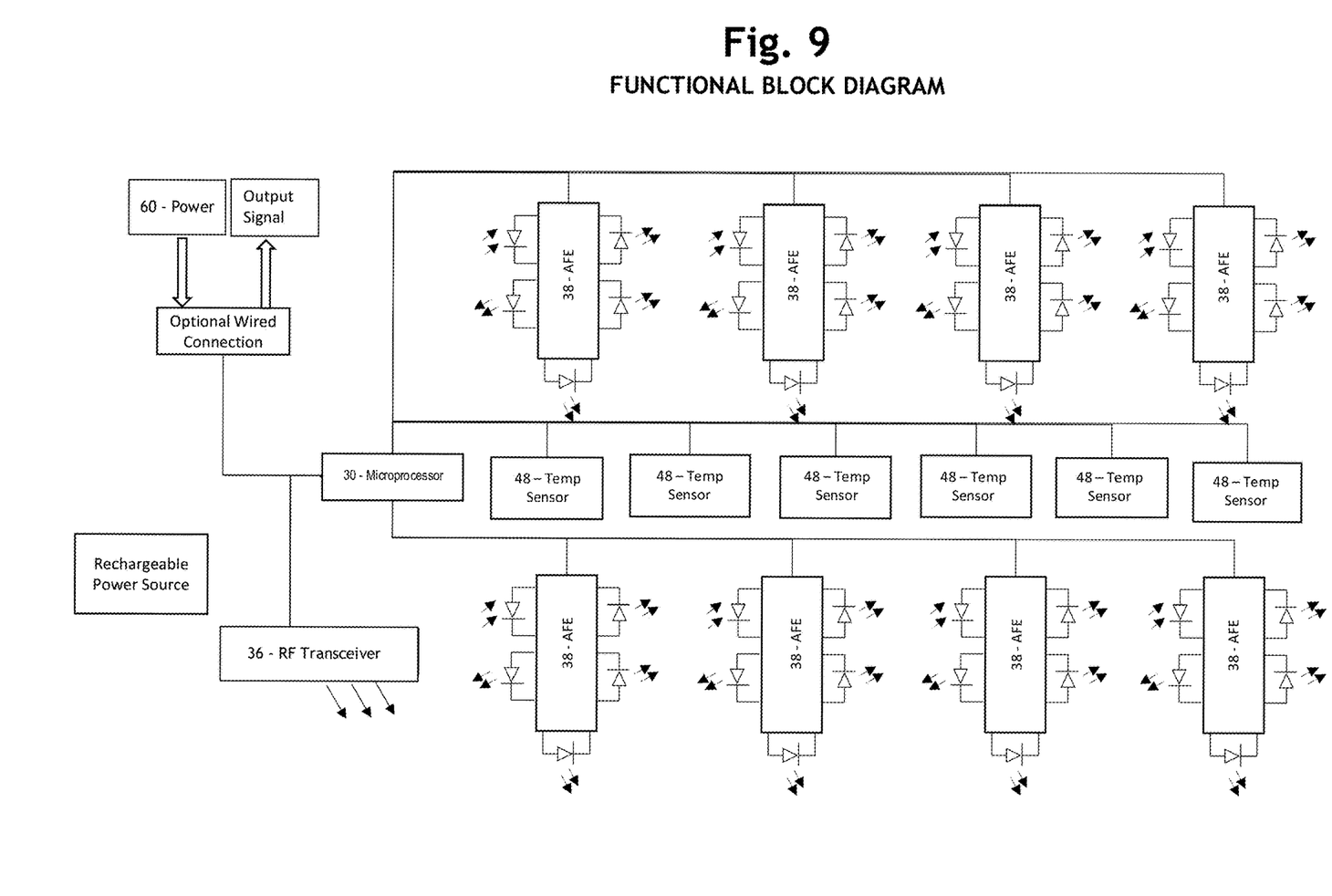
FIG. 9 depicts a simplified functional block diagram of the first preferred embodiment of the wheal and flare analyzing system of FIG. 3, including the cooperative relationships of the microprocessor, the rf transceiver, the analog front end/LED drivers, the temperature sensors, the rechargeable power source, and an optional wired connection.

FIG. 9 depicts a simplified functional block diagram of the first preferred embodiment of the wheal and flare analyzing system of FIG. 3, including the cooperative relationships of the microprocessor, the rf transceiver, the analog front end/LED drivers, the temperature sensors, the rechargeable power source, and an optional wired connection.

Figure 10:
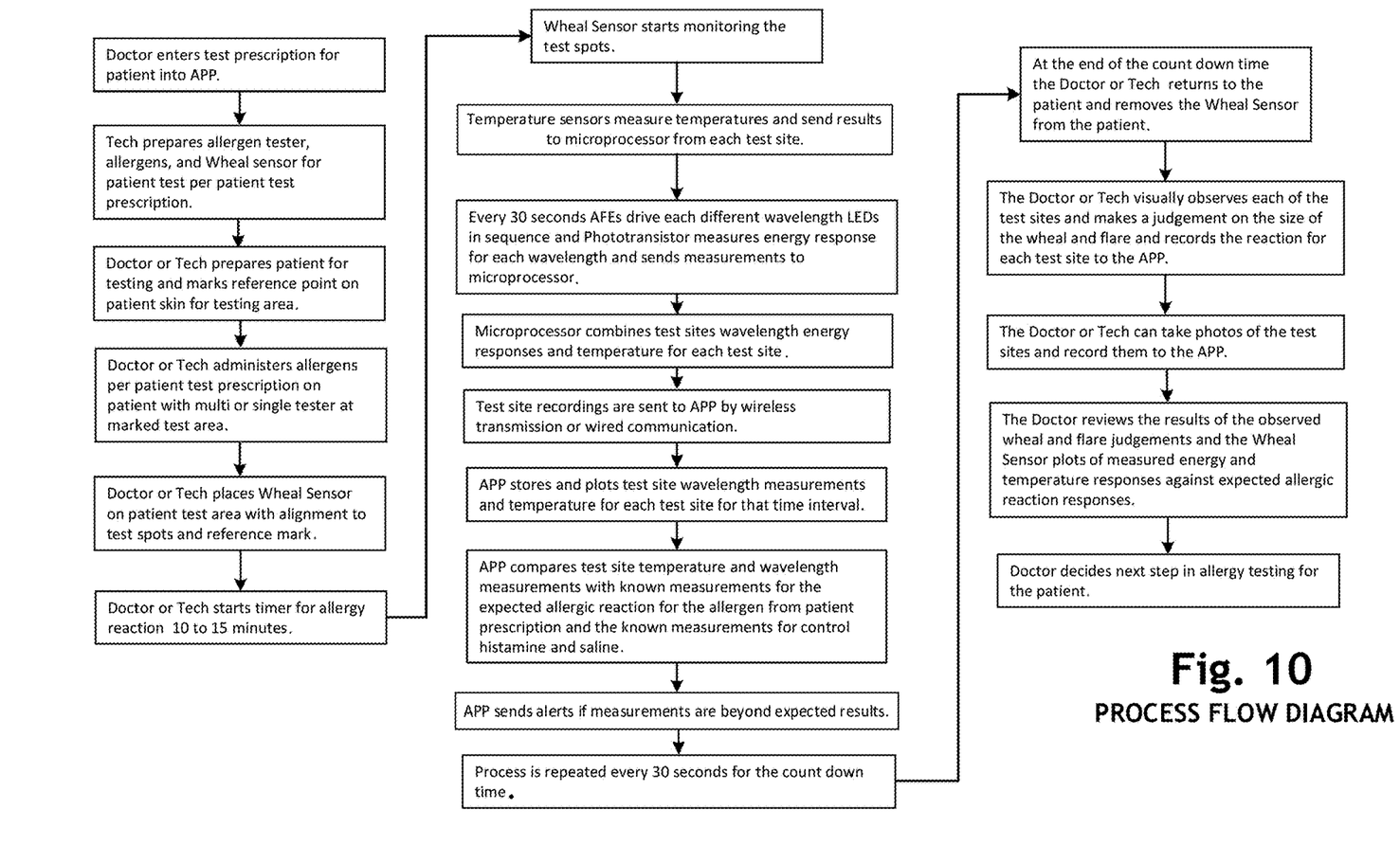
FIG. 10 depicts a simplified process flow diagram of a preferred embodiment of the wheal and flare analyzing system of FIG. 3.

FIG. 10 depicts a simplified process flow diagram of a preferred embodiment of the wheal and flare analyzing system of FIG. 3.

Figure 11:
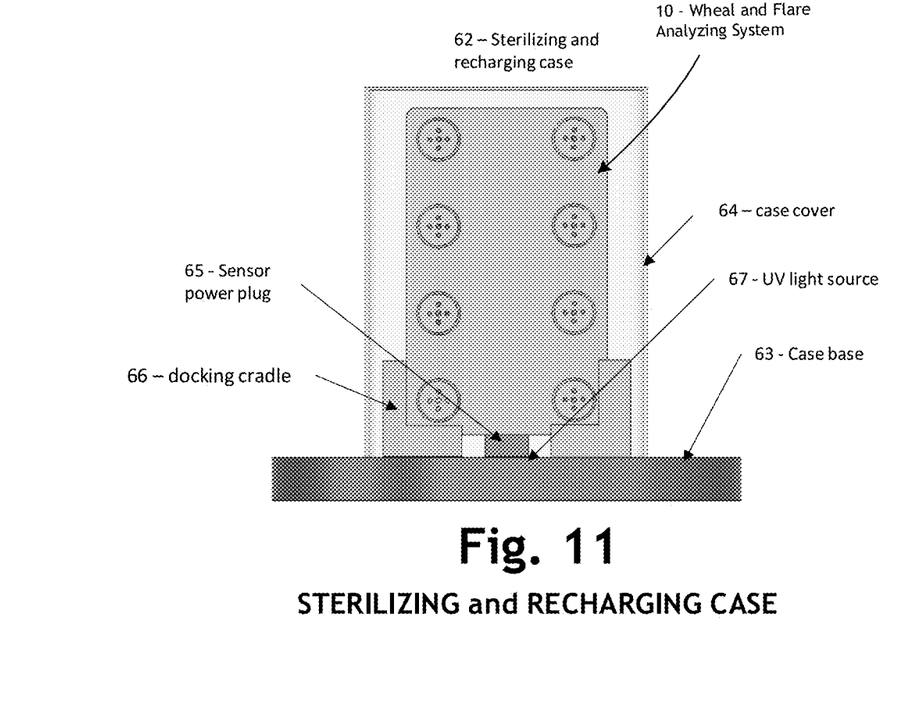
FIG. 11 depicts the wheal and flare analyzing system of FIG. 3 placed in a sterilizing and recharging case.

FIG. 11 depicts the wheal and flare analyzing system [10] placed in a sterilizing and recharging case [62]. The sterilizing and recharging case [62] comprises a case base [63] a docking cradle [66], a sensor power plug [65], UV light source [67], and a case cover [64]. The wheal and flare analyzing system [10] is placed into the sterilizing and recharging case [62] after each use where UV light is introduced inside the closed case by the UV light source [67] to sterilize the wheal and flare analyzing system [10] and recharge the internal power source [60]. Recharging power is transmitted through the communication link and output connector [37] of the wheal and flare analyzing system [10] and the sensor power plug [65] of the sterilizing and recharging case [62]. The sterilizing and recharging case [62] communicates with the system APP that the wheal and flare analyzing system [10] is sterilized, recharged with power, and ready for use.

The allergic reaction [19] can be measured immediately after the application of the allergen and placement of the sensor array [40]. The information is a direct measure of the allergy reaction [19] occurring under the skin. The temperature measurement of the patient skin is also measured to detect an increase in temperature at the reaction sites. The information from the control site is used to compare the information from the other sites as a reference. The information on each site is presented to the doctor to compare against visual observations. A determination of the patient susceptibility to each allergen is determined by the doctor and a course of future action and evaluation is planned.

The wheal and flare analyzing system of the present invention [10] provides information about the reaction immediately after the application and the information is a measurement of the reaction under the skin. The information provides an insight into the amount of reaction over time and the type of reactions that are visible above the skin. The information provides a digital record of the reaction that can be compared to future measurements.

The wheal and flare analyzing system of the present invention [10] enables the amount of allergen applied to the patient to be reduced to produce a measurable reaction.

In addition, the wheal and flare analyzing system of the present invention [10] enables the delivery of the allergen to the tissue requires less penetration of the dermis. This will result in less pain and false positive indications from a wheal created by the histamine release.

Wearable biomedical and health devices are increasing in use and provide valuable information to the wearers. The wheal and flare analyzing system of the present invention [10] uses similar sensing technology but is focused on providing information about allergic reactions after allergy testing is conducted. The testing can be performed in a medical office or at home and self-administered. The data from the wheal and flare analyzing system of the present invention [10] is intended to augment the analysis of medical professionals. The sensor array [40] can be applied to the test sites after the allergens are applied by the previous described scratch or puncture devices. The sensor array [40] can remain in place by gravity when patients are immobile for the time required for the allergic reactions typically 10 to 15 minutes. Additionally, the sensor array [40] can be held in place on the patient by a restraint method such as a belt or strap or an applied adhesive.

The technology in this U.S. patent application is similar to the technology deployed in U.S. patent application Ser. No. 17/688,197, entitled "Produce Freshness Sensor" (C. Bruce Banter), filed on Mar. 7, 2022

Throughout this application, various Provisional Applications, patent applications, and patents are referenced by number and inventor. The disclosures of these documents are hereby incorporated by reference into this specification in their entireties to more fully describe the state of the art to which this invention pertains.

It is evident that many alternatives, modifications, and variations of the wheal and flare analyzing system of the present invention will be apparent to those skilled in the art in lieu of the disclosure herein. It is intended that the metes and bounds of the present invention be determined by the appended claims rather than by the language of the above specification, and that all such alternatives, modifications, and variations which form a conjointly cooperative equivalent are intended to be included within the spirit and scope of these claims.

PARTS LIST

10—Wheal and Flare Analyzing System
12—Antigen
14—Epidermis
15—Dermis
16—Mast Cell
17—Mast Cell-Negative Reaction
18—Mast Cell-Positive Reaction
19—Allergic Reaction
22—Wheal
24—Flare
25—Multiple Applicator Unit
26—Fluid Tray
28—Applicator Tip
29—Reservoir
30—Microprocessor
32—Printed Circuit Board
33—Top Case and
34—Bottom Case
36—RF Transceiver
37—Communications Link
38—Analog Front End
40—Sensor Array
42—Emitter
44—Receiver
48—Temperature Sensor
50—Spacer Ring
51—Reference and Alignment Number
52—Light Guide Emitter
54—Light Guide Receiver
60—Power Source
62—Sterilizing and Recharging Case
63—Case Base
64—Case Cover
65—Sensor Power Plug
66—Docking Cradle
67—UV Light Source

The invention claimed is:

1. A system for analyzing an allergic reaction within mast cells to an allergen being applied in an allergen skin test at an allergen skin test site on skin of a patient, said system comprising:
a sensor array including a first emitter that emits energy of a first wavelength into said skin of said patient, said sensor array including a second emitter that emits energy of a second wavelength into said skin of said patient;
an energy receiver being positionable adjacent to said first emitter and said second emitter, said energy receiver being disposed proximate to said site where said allergen is introduced into said mast cells, said energy receiver measuring said first reflected wavelength from said first emitter, said energy receiver measuring said second reflected wavelength from said second emitter; and
a processor being in digital communication with said first emitter, said second emitter, and said energy receiver, an energy return of said first reflected wavelength and said second reflected wavelength being indicative of intensity of said allergic reaction of said allergen applied to said site in said mast cells.

2. The system of claim 1, wherein said energy receiver is sandwiched between said first and said second emitter.

3. The system of claim 1, further comprising said sensor array having a third emitter that emits energy of a third wavelength into said skin of said patient, a sensor array having a fourth emitter that emits energy of a fourth wavelength into said skin of said patient, said energy receiver being positionable adjacent to said third emitter and said fourth emitter, said energy receiver measuring reflected wavelengths from said third emitter, said energy receiver measuring reflected wavelengths from said fourth emitter, and said processor being in digital communication with said third emitter and said fourth emitter.

4. The system of claim 3, wherein said energy receiver is sandwiched between said third emitter and said fourth emitter.

5. The system of claim 3, wherein said energy receiver is sandwiched between said first emitter and said second emitter is sandwiched between said third emitter and said fourth emitter.

6. The system of claim 1, further comprising said processor being in digital communication with a first temperature sensor, said first temperature sensor measuring a first local dermal temperature, said first local dermal temperature being indicative of said intensity of said allergic reaction to said allergen.

7. The system of claim 1, wherein said sensor array is cooperatively engaged with an analog front end.

8. The system of claim 1, wherein said processor is a microprocessor, said microprocessor, said sensor array, said analog front end, said first emitter, said second emitter, said temperature sensor, and said rf transceiver are mounted on a printed circuit board, said printed circuit board being encapsulated.

9. The system of claim 1, further comprising a recharging unit for recharging an internal power source after each use.

10. The system of claim 1, further comprising a sterilizing unit, where UV light source is introduced inside the sterilizing unit to sterilize the wheal and flare analyzing system after use.

11. A method for analyzing an allergic reaction within mast cells to an allergen being administered in an allergen skin test site onto skin of a patient, said method comprising:
emitting energy of various wavelengths from a sensor array into said skin of said patient, said sensor array having a first emitter and a second emitter, said first emitter being disposed proximate to said second emitter;
measuring reflected wavelengths from said first and second emitter with an energy receiver, said energy receiver being disposed proximate to said first emitter and said second emitter, said energy receiver measuring reflected wavelengths from said first emitter, said energy receiver measuring reflected wavelengths from said second emitter; and
determining intensity of said allergic reaction to said allergen in said mast cells with a processor, said processor being in digital communication with said first and said second emitter and said energy receiver, an energy return of said first reflected wavelength and said second reflected wavelength being indicative of intensity of said allergic reaction of said allergen applied to said site in said mast cells.

12. The method of claim 11, further comprising measuring temperature at a first local dermal site with a first temperature sensor, said first dermal site being proximate to said allergen skin test site, said first temperature sensor being in digital communication with said processor, said first local dermal temperature being indicative of said intensity of said allergic reaction to said allergen.

13. The method of claim 11, wherein said energy receiver is sandwiched between said first emitter and said second emitter.

14. The method of claim 11, further comprising said sensor array having a third emitter that emits energy of a third wavelength into said skin of said patient, said sensor array having a fourth emitter that emits energy of a fourth wavelength into said skin of said patient, said energy receiver being positionable adjacent to said third emitter and said fourth emitter, said energy receiver measuring reflected wavelengths from said third emitter, said energy receiver measuring reflected wavelengths from said fourth emitter, and said processor being in digital communication with said third emitter and said fourth emitter.

15. The method of claim 11, further comprising said sensor array having a third emitter that emits energy of a third wavelength into said skin of said patient, said sensor array having a fourth emitter that emits energy of a fourth wavelength into said skin of said patient, said energy receiver being sandwiched between said third emitter and said fourth emitter.

16. A method for analyzing an allergic reaction within mast cells to an allergen being applied in an allergen skin test at a site on skin of a patient, said method comprising:
providing a sensor array including a first emitter that emits energy having a first wavelength into said skin of said patient, said sensor array including a second emitter that emits energy having a second wavelength into said skin of said patient;
providing an energy receiver being positionable adjacent to said first emitter and said second emitter, said energy receiver being disposed proximate to said site where said allergen is introduced into said mast cells, said energy receiver measuring said first reflected wavelength from said first emitter, said energy receiver measuring said second reflected wavelength from said second emitter; and
providing a processor that is in digital communication with said first emitter, said second emitter, and said energy receiver, an energy return of said first reflected wavelength and said second reflected wavelength being indicative of intensity of said allergic reaction of said allergen applied to said site in said mast cells.

17. The method of claim 16, further comprising measuring temperature at a first local dermal site with a first temperature sensor, said first dermal site being proximate to said allergen skin test site, said first temperature sensor being in digital communication with said processor, said first local dermal temperature being indicative of said intensity of said allergic reaction to said allergen.

18. The method of claim 16, wherein said energy receiver is sandwiched between said first emitter and said second emitter.

19. The method of claim 16, further comprising said sensor array having a third emitter that emits energy of a third wavelength into said skin of said patient, said sensor array having a fourth emitter that emits energy of a fourth wavelength into said skin of said patient, said energy receiver being positionable adjacent to said third emitter and said fourth emitter, said energy receiver measuring reflected wavelengths from said third emitter, said energy receiver measuring reflected wavelengths from said fourth emitter, and said processor being in digital communication with said third emitter and said fourth emitter.

20. The method of claim 16, further comprising said sensor array having a third emitter that emits energy of a third wavelength into said skin of said patient, said sensor array having a fourth emitter that emits energy of a fourth wavelength into said skin of said patient, said energy receiver being sandwiched between said third emitter and said fourth emitter.

* * * * *